US008916444B2

(12) United States Patent
Goto et al.

(10) Patent No.: US 8,916,444 B2
(45) Date of Patent: Dec. 23, 2014

(54) NON-UNIFORM CHANNEL JUNCTION-LESS TRANSISTOR

(71) Applicant: Taiwan Semiconductor Manufacturing Company, Ltd., Hsinchu (TW)

(72) Inventors: Ken-Ichi Goto, Hsin-Chu (TW); Zhiqiang Wu, Chubei (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 13/941,199

(22) Filed: Jul. 12, 2013

(65) Prior Publication Data
US 2014/0024182 A1 Jan. 23, 2014

Related U.S. Application Data

(62) Division of application No. 13/077,144, filed on Mar. 31, 2011, now Pat. No. 8,487,378.

(60) Provisional application No. 61/434,963, filed on Jan. 21, 2011.

(51) Int. Cl.
H01L 21/336 (2006.01)
H01L 29/66 (2006.01)
G01N 33/68 (2006.01)
H01L 29/78 (2006.01)

(52) U.S. Cl.
CPC ... *H01L 29/66803* (2013.01); *H01L 2029/7857* (2013.01); *G01N 33/6893* (2013.01); *H01L 29/785* (2013.01)
USPC ............ 438/305; 438/163; 438/142; 438/197

(58) Field of Classification Search
CPC . H01L 21/336; H01L 29/6659; H01L 29/665; H01L 29/6656
USPC .......... 438/142, 197, 163, 305; 257/347, 288, 257/E21.409, E29.242
See application file for complete search history.

(56) References Cited

U.S. PATENT DOCUMENTS

| | | | | |
|---|---|---|---|---|
| 7,687,859 B2 * | 3/2010 | Russ et al. | .................... | 257/357 |
| 2004/0256647 A1 * | 12/2004 | Lee et al. | ....................... | 257/289 |
| 2010/0207211 A1 * | 8/2010 | Sasaki et al. | .................. | 257/347 |
| 2012/0187486 A1 | 7/2012 | Goto et al. | | |

OTHER PUBLICATIONS

E. R. Hsieh et al., "A New Type of Inverter with Junctionless (J-Less) Transistors", 2 pages.

(Continued)

*Primary Examiner* — Timor Karimy
(74) *Attorney, Agent, or Firm* — Haynes and Boone, LLP

(57) ABSTRACT

The present disclosure discloses a method of forming a semiconductor layer on a substrate. The method includes patterning the semiconductor layer into a fin structure. The method includes forming a gate dielectric layer and a gate electrode layer over the fin structure. The method includes patterning the gate dielectric layer and the gate electrode layer to form a gate structure in a manner so that the gate structure wraps around a portion of the fin structure. The method includes performing a plurality of implantation processes to form source/drain regions in the fin structure. The plurality of implantation processes are carried out in a manner so that a doping profile across the fin structure is non-uniform, and a first region of the portion of the fin structure that is wrapped around by the gate structure has a lower doping concentration level than other regions of the fin structure.

20 Claims, 18 Drawing Sheets

(56) References Cited

OTHER PUBLICATIONS

Jean-Pierre Colinge et al., "Analysis of the Junctionless Transistor Architecture", Extended Abstract of the 2010 International Conference on Solid State Devices and Materials, Tokyo 2010, pp. 1042-1043.

Chi-Woo Lee et al., "Performance Estimation of Junctionless Multigate Transistors", Solid State Electronics 54 (2010) pp. 97-103.

* cited by examiner

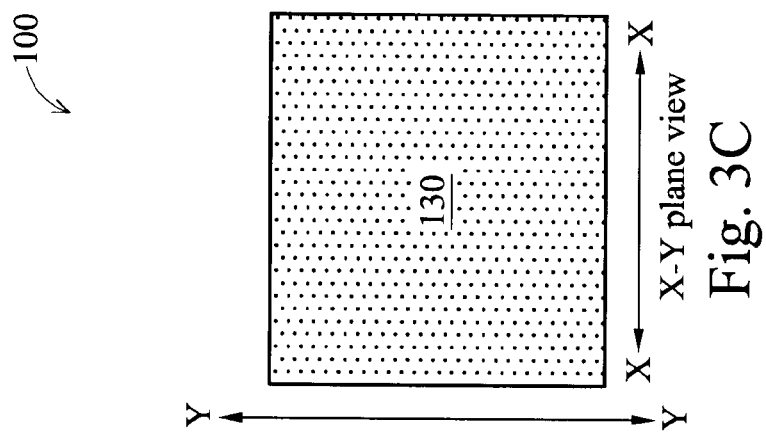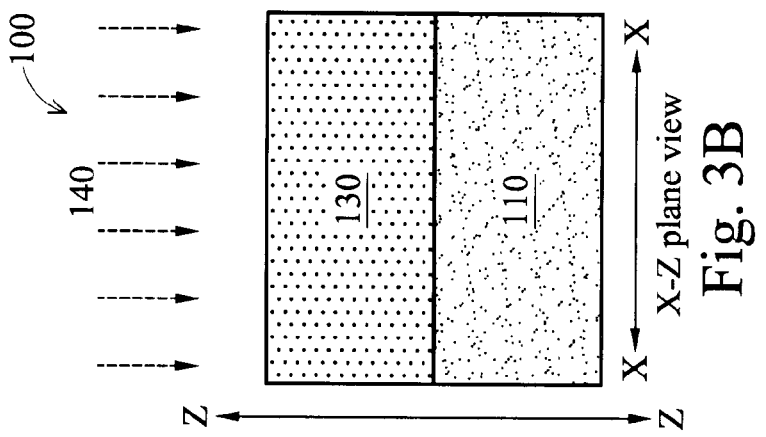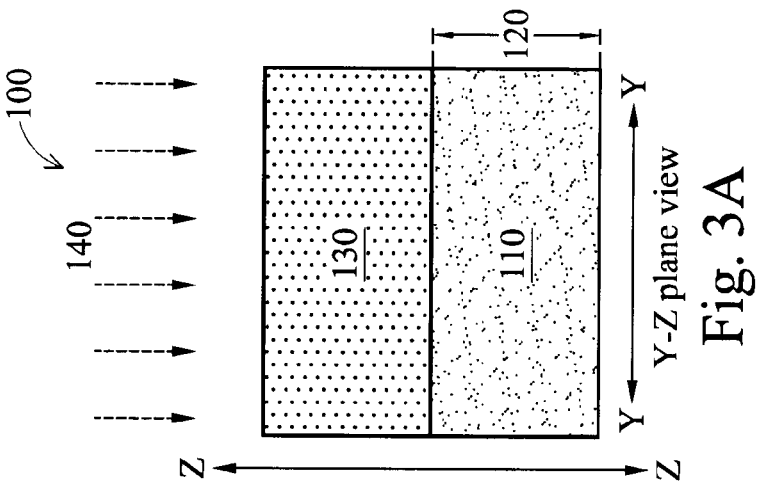

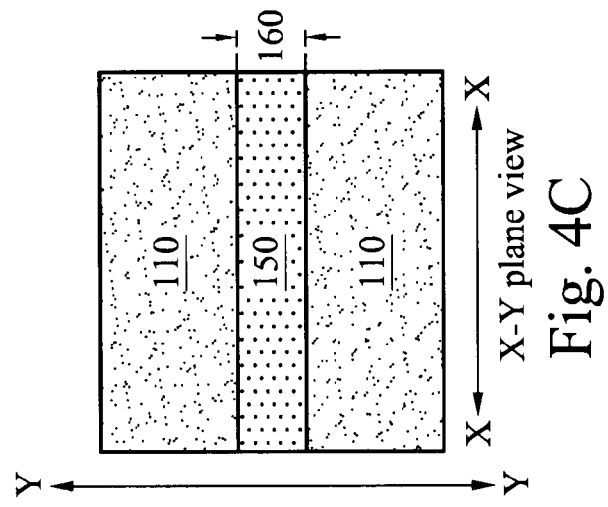
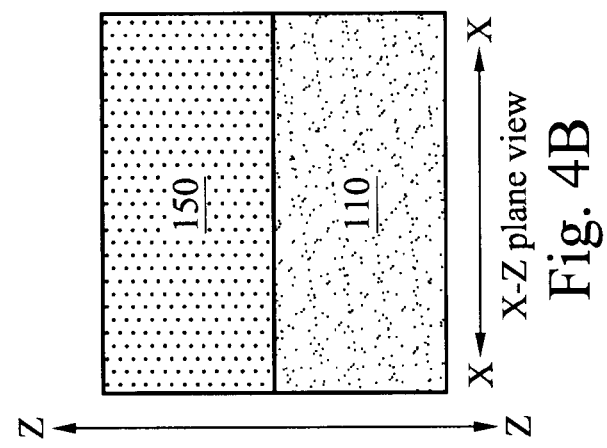
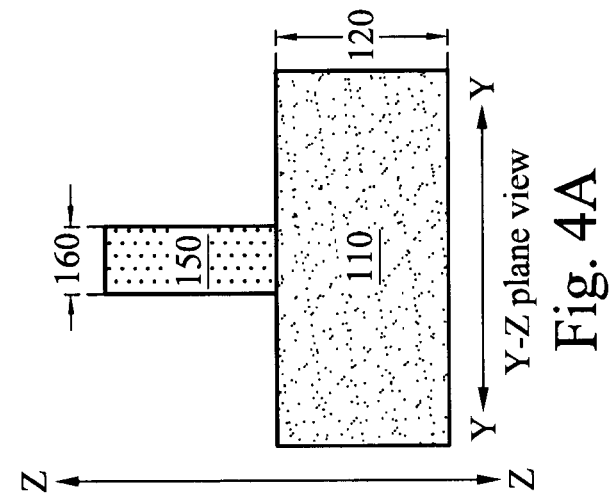

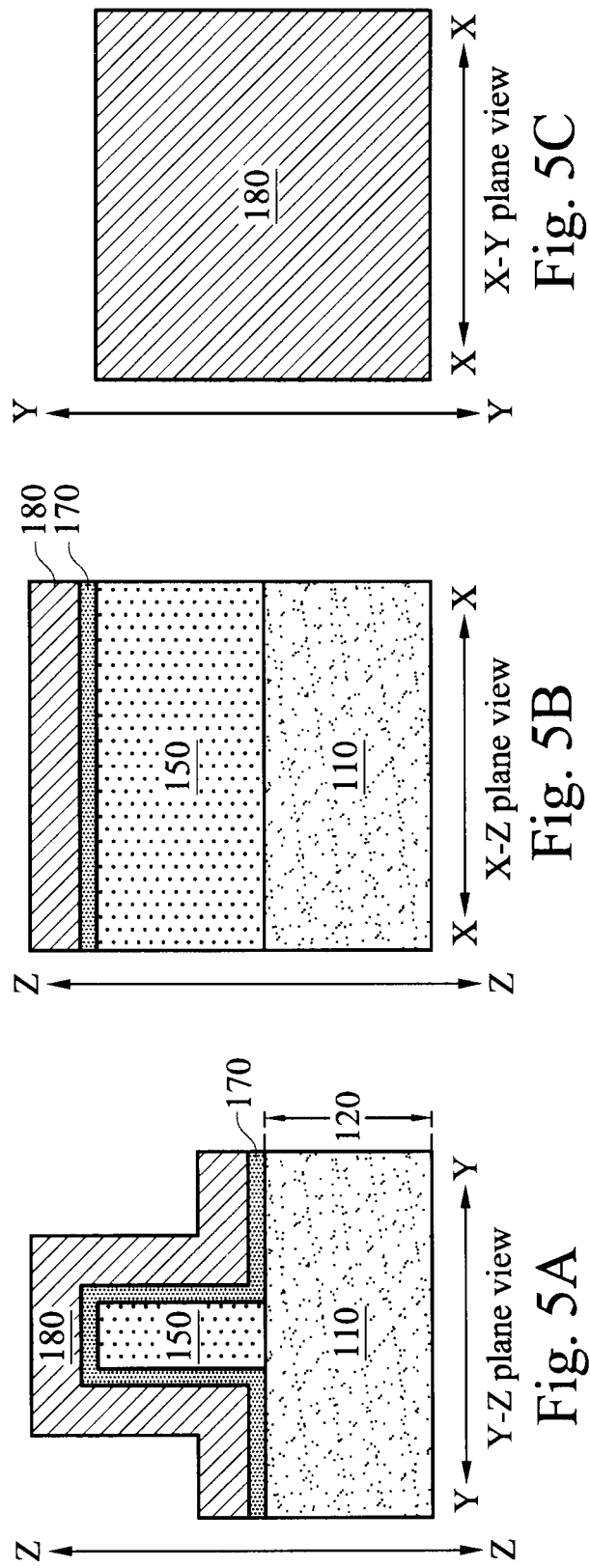

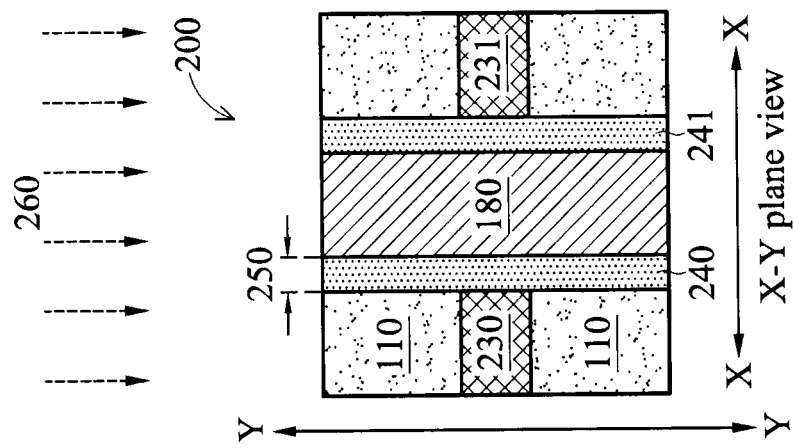
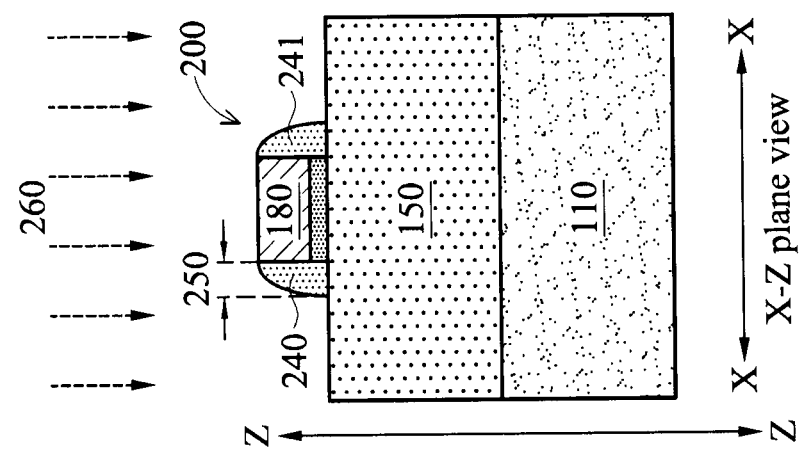
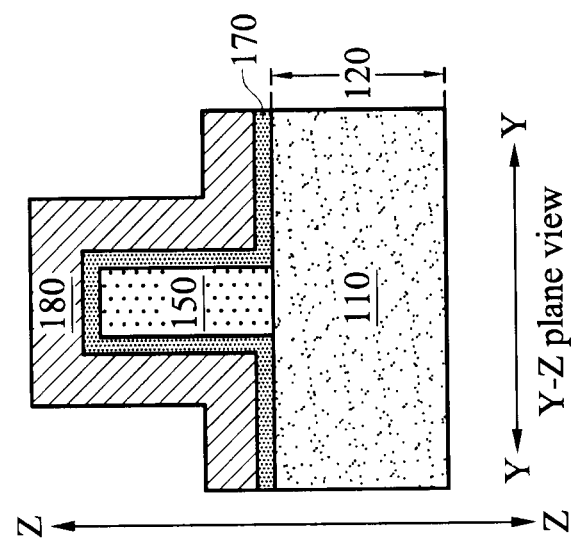
Fig. 7C
Fig. 7B
Fig. 7A

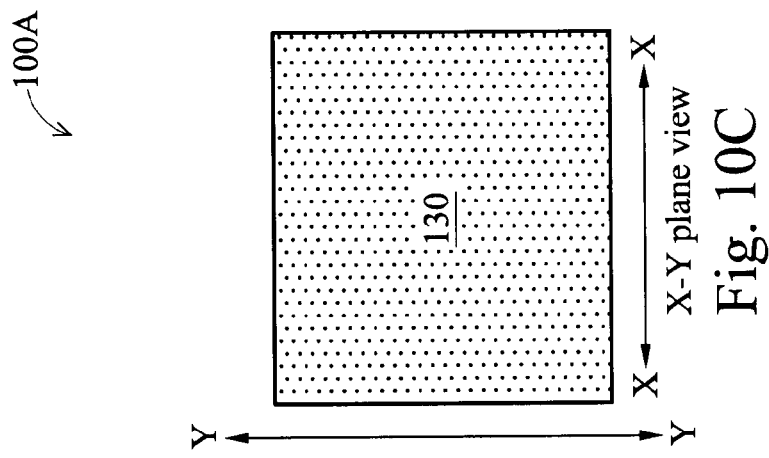
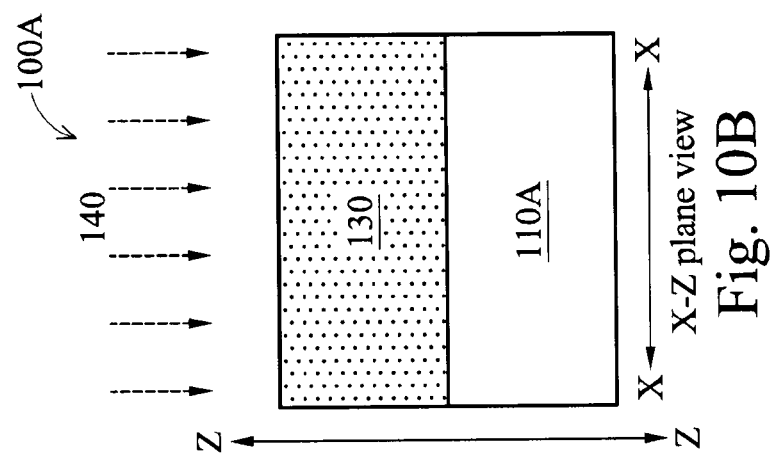
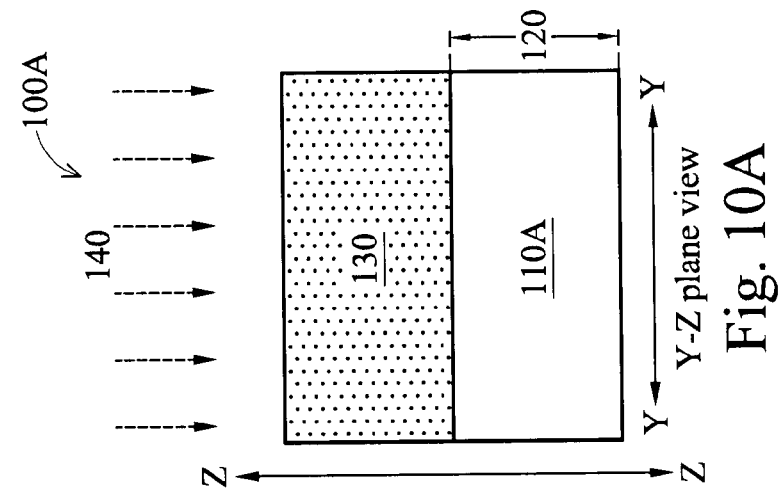

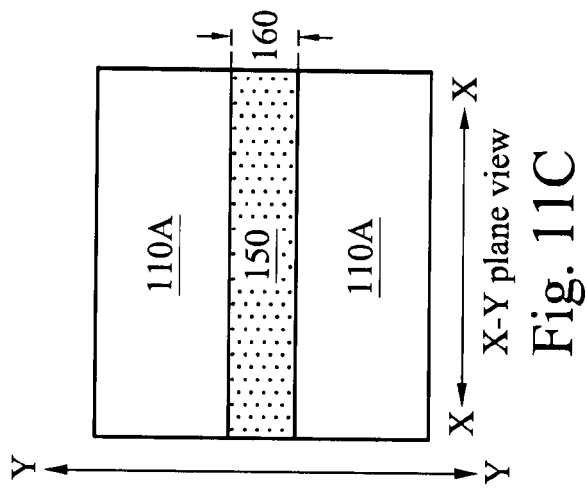
Fig. 11C X-Y plane view
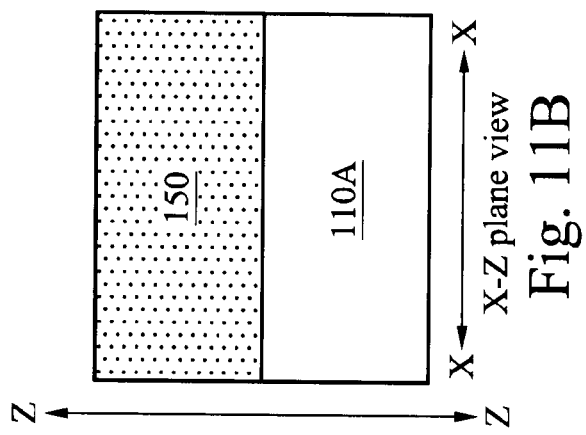
Fig. 11B X-Z plane view
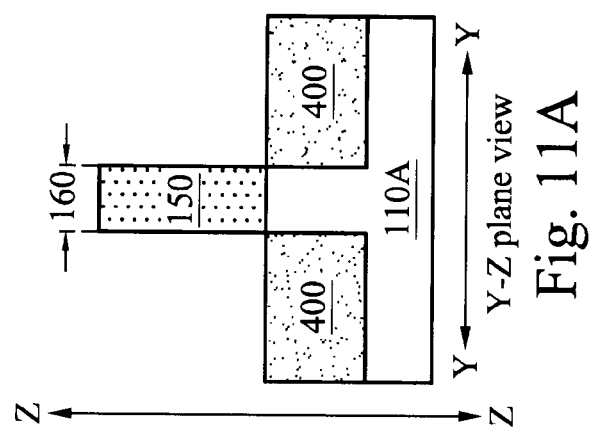
Fig. 11A Y-Z plane view

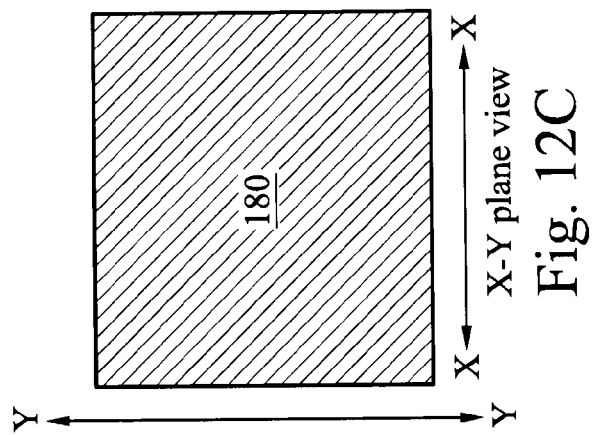
Fig. 12C X-Y plane view
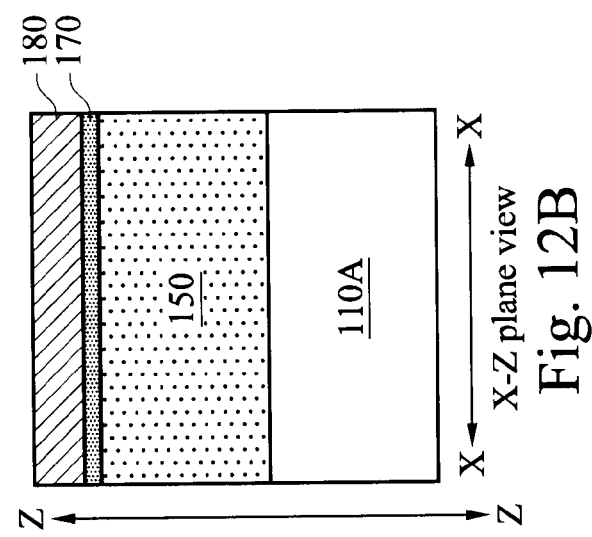
Fig. 12B X-Z plane view
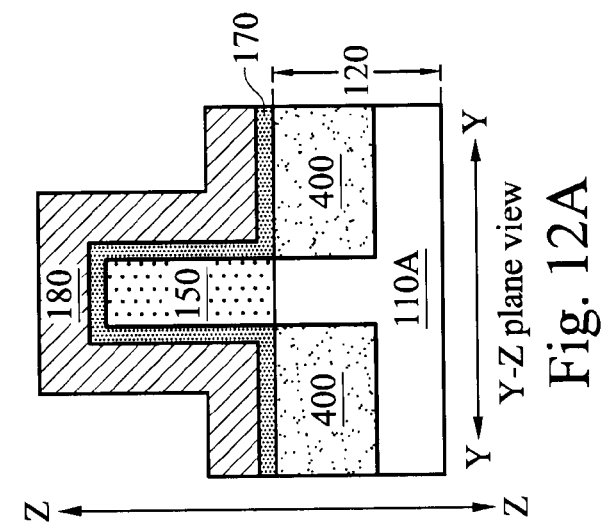
Fig. 12A Y-Z plane view

NON-UNIFORM CHANNEL JUNCTION-LESS TRANSISTOR

PRIORITY DATA

This application is a divisional application of U.S. application Ser. No. 13/077,144, filed Mar. 31, 2011 which claims priority to U.S. Application No. 61/434,963, filed on Jan. 21, 2011, entitled "Non-Uniform Channel Junction-Less Transistor," the entire disclosures of which are incorporated herein by reference.

BACKGROUND

The semiconductor industry has progressed into nanometer technology process nodes in pursuit of higher device density, higher performance, and lower costs. As this progression takes place, challenges from both fabrication and design issues have resulted in the development of three-dimensional designs, such as fin-like field effect transistor (FinFET) device. A typical FinFET device is fabricated with a thin "fin" (or fin-like structure) extending from a substrate. The fin usually includes silicon and forms the body of the transistor device. The channel of the transistor is formed in this vertical fin. A gate is provided over (e.g., wrapping around) the fin. This type of gate allows greater control of the channel. Other advantages of FinFET devices include reduced short channel effect and higher current flow. However, for conventional FinFET devices, the amount of drain current of FinFET devices may be adversely impacted by high parasitic resistance.

Therefore, while existing methods of fabricating FinFET devices have been generally adequate for their intended purposes, they have not been entirely satisfactory in every aspect.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

FIGS. 3A-C, 4A-4C, 5A-5C, 6A-6C, 7A-7C, and 8 are diagrammatic fragmentary cross-sectional and top level views of a FinFET device at different stages fabrication in accordance with an embodiment of the present disclosure.

FIGS. 10A-C, 11A-11C, 12A-12C, 13A-13C, and 14A-14C are diagrammatic fragmentary cross-sectional and top level views of a FinFET device at different stages fabrication in accordance with an alternative embodiment of the present disclosure.

DETAILED DESCRIPTION

Figure 1:
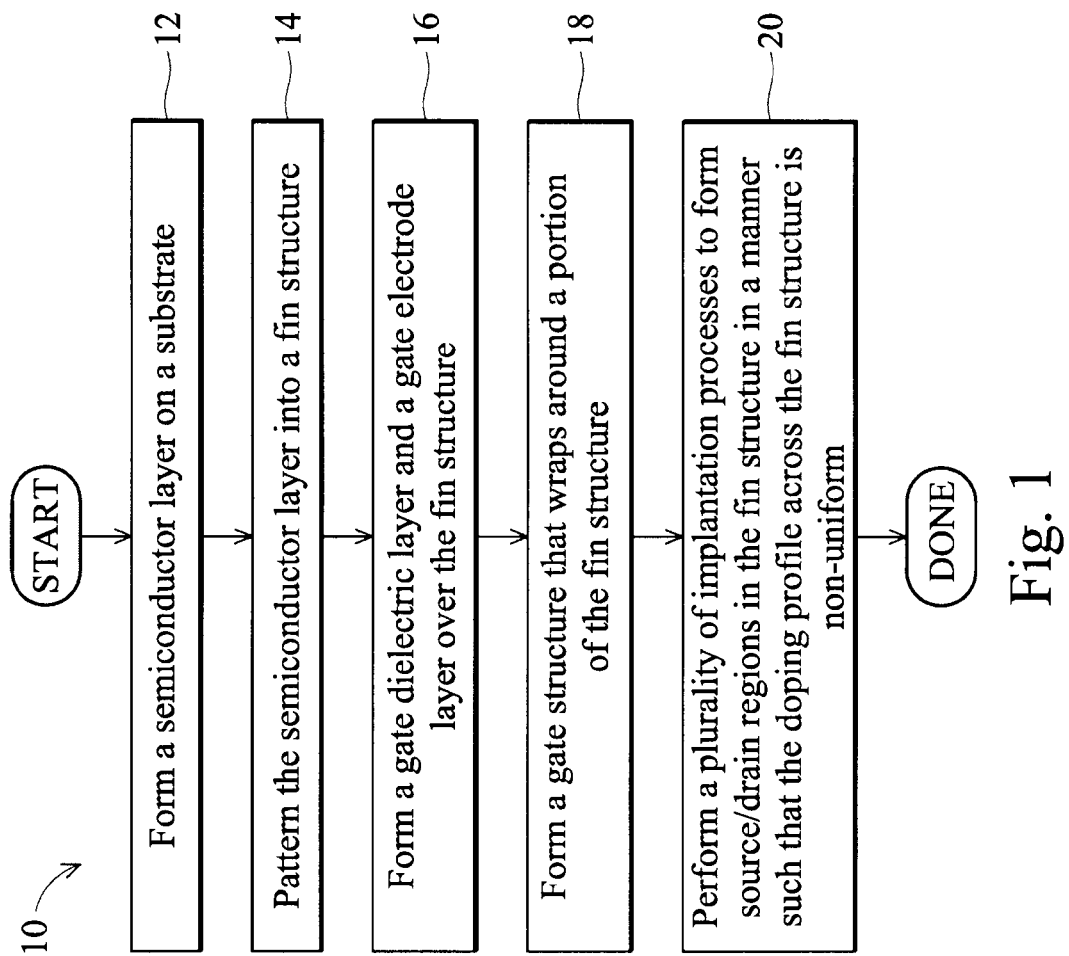
FIG. 1 is a flow chart of a method for fabricating a FinFET device in accordance with aspects of the present disclosure.

It is understood that the following disclosure provides many different embodiments, or examples, for implementing different features of the invention. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the sake of simplicity and clarity and does not in itself dictate a relationship between the various embodiments and/or configurations discussed. Moreover, various features may be arbitrarily drawn in different scales for the sake of simplicity and clarity.

FIG. 1 is a flowchart of a method 10 for fabricating a FinFET device in accordance with various aspects of the present disclosure. The method 10 begins with block 12 in which a semiconductor layer is formed on a substrate. The method 10 continues with block 14 in which the semiconductor layer is patterned into a fin structure. The method 10 continues with block 16 in which a gate dielectric layer and a gate electrode layer are formed over the fin structure. The method 10 continues with block 18 in which the gate dielectric layer and the gate electrode layer are patterned to form a gate structure in a manner so that the gate structure wraps around a portion of the fin structure. The method 10 continues with block 20 in which a plurality of implantation processes are performed to form source/drain regions in the fin structure on either side of the gate structure. The plurality of implantation processes are carried out in a manner so that a doping profile across the fin structure is non-uniform. A portion of the fin structure directly underneath the gate structure has a lower doping concentration than the rest of the fin structure.

Figure 2:
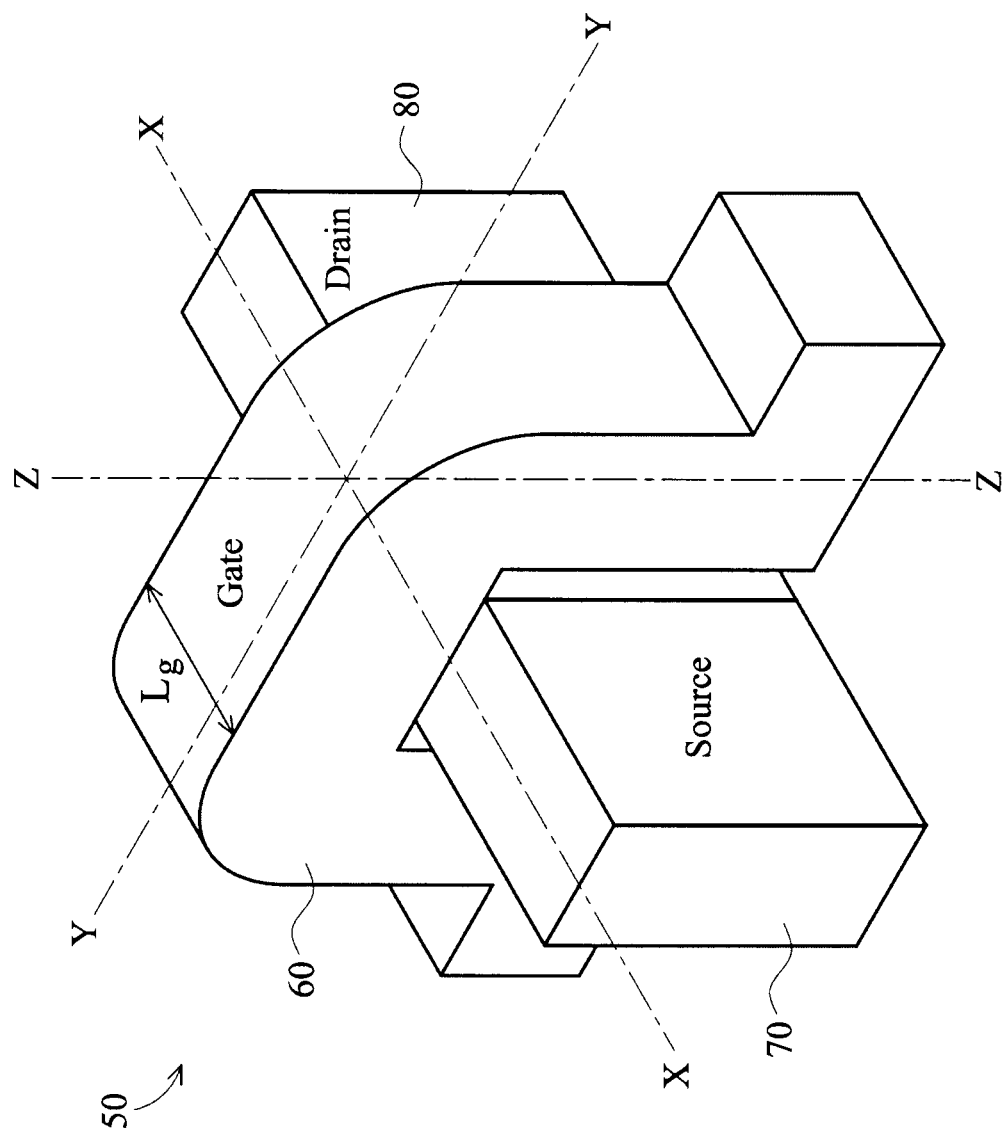
FIG. 2 is a perspective view of an example FinFET device.

The use of FinFET devices has been gaining popularity in the semiconductor industry. Referring to FIG. 2, a perspective view of an example FinFET device 50 is illustrated. The FinFET device 50 is a non-planar multi-gate transistor that is built on a substrate. A thin silicon "fin-like" structure (referred to as fin) forms the body of the FinFET device 50. A gate 60 of the FinFET device 50 is wrapped around this fin. Lg denotes a length (or width, depending on the perspective) of the gate 60. A source 70 and a drain 80 of the FinFET device 50 are formed in extensions of the fin on opposite sides of the gate 60. The fin itself serves as a channel. The effective channel length of the FinFET device 50 is determined by the dimensions of the fin.

FinFET devices offer several advantages over traditional Metal-Oxide Semiconductor Field Effect Transistor (MOSFET) devices (also referred to as planar devices). These advantages may include better chip area efficiency, improved carrier mobility, and fabrication processing that is compatible with the fabrication processing of planar devices. Thus, it may be desirable to design an integrated circuit (IC) chip using FinFET devices for a portion of, or the entire IC chip.

However, traditional FinFET devices may have an uniform channel profile and thus may suffer from high parasitic resistance, which may adversely affect the magnitude of the drain current. Here, the various aspects of the present disclosure involve forming a FinFET device having a non-uniform channel profile and consequently has a reduced parasitic resistance. Therefore, the FinFET device fabricated according to the present disclosure has improved drain current performance. The following Figures illustrate various cross-sectional views and top views of a FinFET device at different stages of fabrication. For the sake of clarity, three-dimensional axes X, Y, and Z are shown in FIG. 2 to correspond to the axes in the later Figures. The X, Y, and Z axes may also be referred to as the X, Y, and Z directions, respectively.

Referring now to FIGS. 3A, 3B, and 3C, FIG. 3A is a cross-sectional view of a FinFET device 100 taken at the Y-Z plane, FIG. 3B is a cross-sectional view of the FinFET device 100 taken at the X-Z plane, and FIG. 3C is a top view of the FinFET device 100 taken at the X-Y plane. The FinFET device 100 includes a substrate 110. In an embodiment, the substrate 110 includes a dielectric material, for example silicon oxide ($SiO_2$). The substrate 110 has a thickness 120. In an embodiment, the thickness is in a range from about 4 nanometers (nm) to about 30 nm.

A semiconductor layer 130 is formed on the substrate 110. In an embodiment, the semiconductor layer 130 includes a crystal silicon material. It is understood that the semiconductor layer 130 may include other suitable materials in alternative embodiments. An implantation process 140 is performed on the semiconductor layer 130 to implant a plurality of dopant ions to the semiconductor layer 130. The dopant ions include an N-type material in an embodiment, for example arsenic (As) or phosphorous (P). After the implantation process 140 is performed, a doping concentration level is in a range from about $1\times10^{17}$ ions/cm$^3$ to about $5\times10^{19}$ ions/cm$^3$. In other embodiments, the dopant ions may include a P-type material, for example boron (B), and the doping concentration levels may be different.

Referring now to FIGS. 4A-4C, the semiconductor layer 130 is patterned to form a fin structure 150. The fin structure 150 extends in an elongate manner along the X direction, as illustrated in FIGS. 4B and 4C. As discussed previously, the fin structure 150 will serve as a conductive channel for the FinFET device 100. The fin structure 150 has a fin width 160 measured in the Y direction. In an embodiment, the fin width 160 is in a range from about 2 nm to about 15 nm.

Referring now to FIGS. 5A-5C, a gate dielectric layer 170 is formed around the fin structure 150, and a gate electrode layer 180 is formed on the gate dielectric layer 170. The gate dielectric layer 170 and the gate electrode layer 180 may each be formed using a deposition process known in the art, for example chemical vapor deposition (CVD), physical vapor deposition (PVD), atomic layer deposition (ALD), combinations thereof, or another suitable process. In an embodiment, the gate dielectric layer 170 includes a hafnium oxide ($HfO_2$) material and has a thickness (measured in the Z direction) that is in a range from about 1 nm to about 3 nm. In an embodiment, the gate electrode layer 180 includes a titanium nitride (TiN) material and has a thickness (measured in the Z direction) that is in a range from about 1 nm to about 20 nm.

Figure 6C:
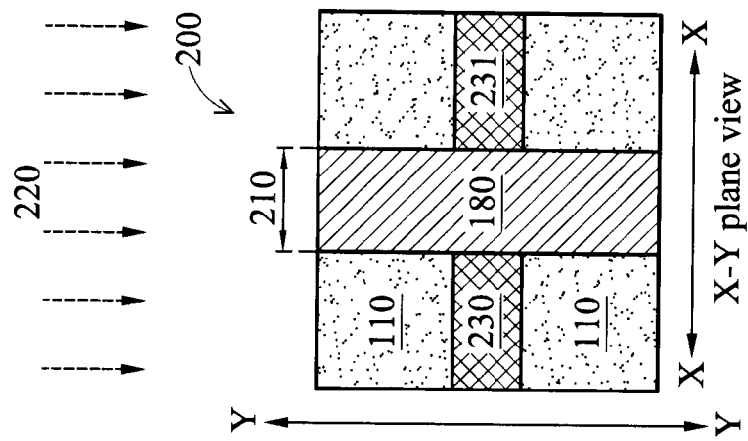
Figure 6B:
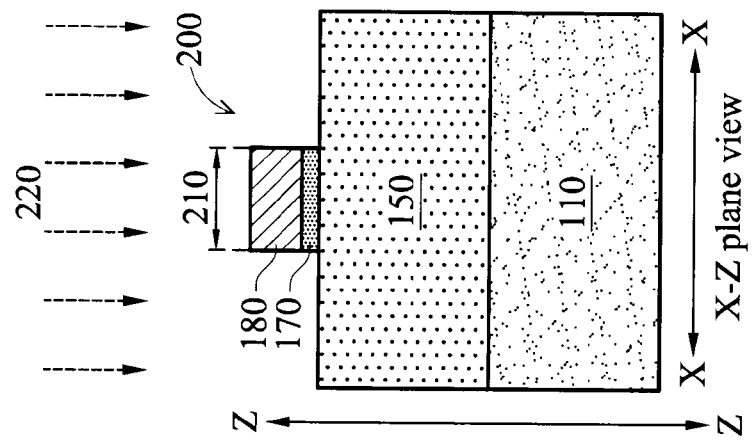
Figure 6A:
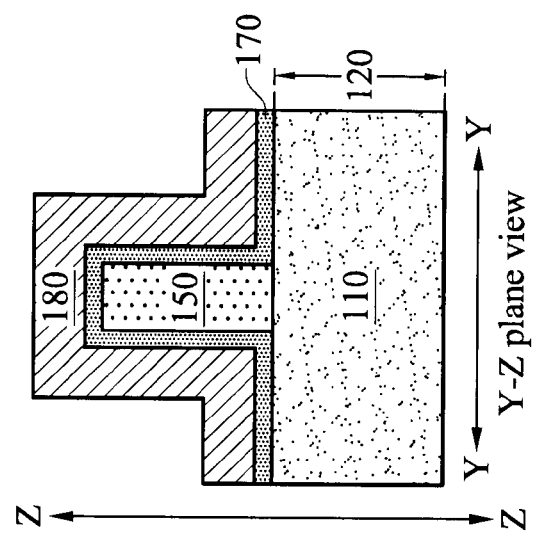

Referring now to FIGS. 6A-6C, the gate electrode layer 180 and the gate dielectric layer 170 undergo a patterning process to form a gate structure 200. The gate structure 200 extends in an elongate manner along the Y direction, as illustrated in FIGS. 6A and 6C. The gate structure 200 wraps around a portion of the fin structure 150. The portion of the fin structure 150 being wrapped around by the gate structure 200 constitute a conductive channel region 205 according to an embodiment. The gate structure 200 has a width 210 that is measured in the X direction, as illustrated in FIGS. 6A and 6C. In an embodiment, the width 210 is in a range from about 2 nm to about 15 nm.

After the gate structure 200 is formed, an implantation process 220 is performed to implant dopant ions into portion of the fin structure 150 (the patterned-semiconductor layer 130) located on either (or opposite) side of the gate structure 200, thereby forming source/drain regions 230-231. The dopant ions have the same doping polarity as the dopant ions used in the implantation process 140. For example, in an embodiment where an N-type dopant is used for the implantation process 140, an N-type dopant is used for the implantation process 220 as well. In an embodiment, the implantation process 220 has a higher dosage than the implantation process 140, and consequently the doping concentration level of the source/drain regions 230-231 is higher than that of the channel region 205 (portion of the fin structure 150 being wrapped around by the gate structure 200). In an embodiment, the doping concentration level of the source/drain regions 230-231 is in a range from about $1\times10^{18}$ ions/cm$^3$ to about $1\times10^{20}$ ions/cm$^3$.

Referring now to FIGS. 7A-7C, gate spacers 240 and 241 are formed around the long sides of gate structure 200. In other words, the spacers 240-241 extend in an elongate manner along the Y direction. The gate spacers 240-241 are formed by depositing a spacer material over the gate structure 200 and thereafter performing a patterning process (for example an etching process) on the spacer material. The spacer material may include a dielectric material. In an embodiment, the spacer material includes silicon oxide or silicon nitride. The spacers 240-241 each have a width 250 that is measured in the X direction. In an embodiment, the width 250 is in a range from about 2 nm to about 20 nm.

After the spacers 240-241 are formed, an implantation process 260 is performed to implant dopant ions into portion of the fin structure 150 not covered by the spacers 240-241 or the gate structure 200. This implantation process 260 is part of the formation process of the source/drain regions 230-231. The dopant ions have the same doping polarity as the dopant ions used in the implantation processes 140 and 220. For example, in an embodiment where an N-type dopant is used for the implantation processes 140 and 220, an N-type dopant is used for the implantation process 260 as well. In an embodiment, the implantation process 260 has a higher dosage than the implantation process 220, and consequently the doping concentration level of the source/drain regions 230-231 not underneath the spacers 240-241 is higher than that of the source/drain regions underneath the spacers 240-241. In an embodiment, the doping concentration level of the portions of the source/drain regions 230-231 not covered by the gate structure 200 or the spacers 240-241 is in a range from about $1\times10^{20}$ ions/cm$^3$ to about $1\times10^{21}$ ions/cm$^3$.

It is understood that an epitaxial growth process may replace the implantation process 260 in an alternative embodiment. Furthermore, an activation annealing process may be subsequently performed, which may have a temperature range from about 900 degrees Celsius to about 1050 degrees Celsius, and a process duration of less than about 1 second.

Based on the discussions above, it can be seen that the fin structure 150 has a non-uniform doping concentration profile. Due to the various implantation processes discussed above, the doping concentration levels decrease (although not necessarily linearly) as it gets closer to the center directly beneath the gate structure 200. For the purposes of providing a clearer illustration, FIG. 8 provides a more detailed view of the cross-sectional view of FIG. 7B (taken at the X-Z plane).

Figure 8:
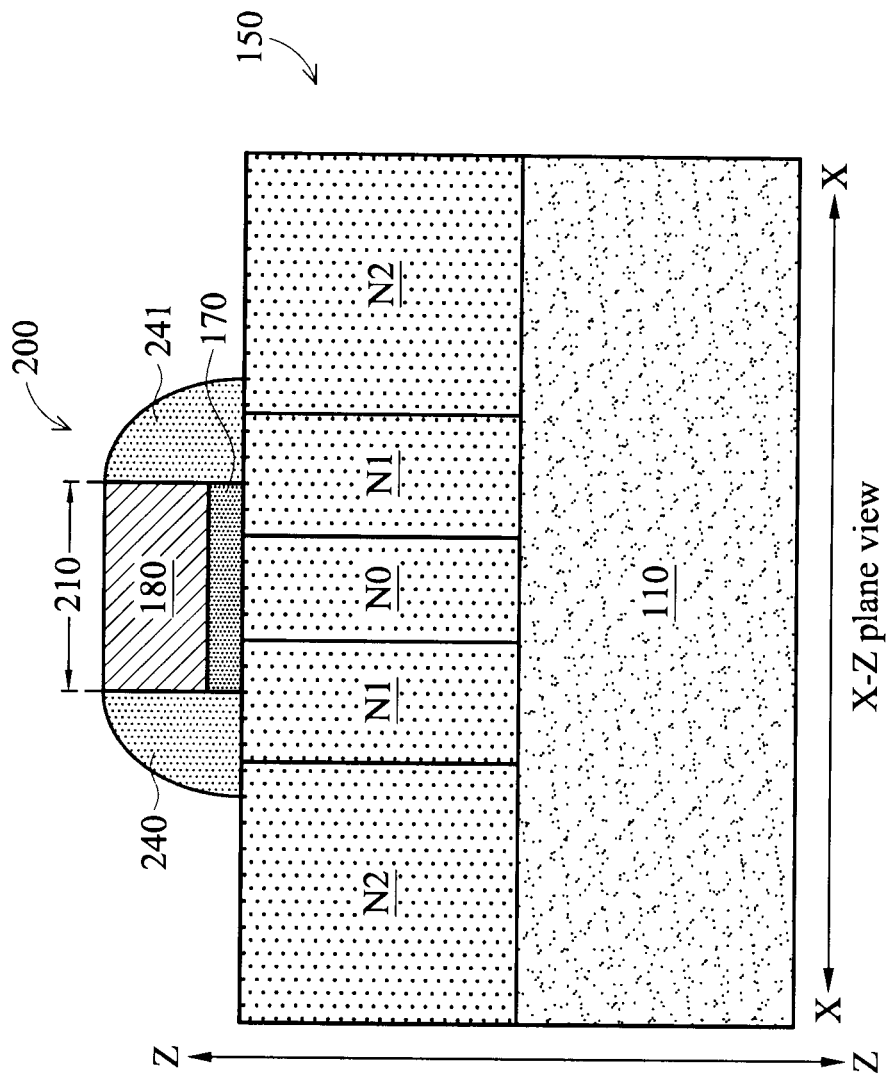

Referring to FIG. 8, the fin structure 150 includes three regions designated at N0, N1, and N2. The region N0 is located beneath the center of the gate structure 200 and has the lowest doping concentration level. The region N1 includes two portions and are located on opposite sides of the region N0. The region N1 has a higher doping concentration level than N0. In some embodiments, the region N1 includes the lightly doped source/drain (LDD) region. The region N2 includes two portions that are located on opposite sides of the region N1. The region N2 has a higher doping concentration level than both the regions N0 and N1. In some embodiments, the region N2 includes the source/drain (S/D) regions. Note that the regions N0, N1, N2 may not exactly align with the sidewalls of the gate structure 220 or the edges of the spacers 240-241. For example, the region N2 may extend underneath the spacers 240-241, and the region N1 may extend underneath the gate dielectric layer 170.

The region N0 has a width 270, the region N1 has a width 280, and the region N1 has an overlapping distance 290 with the gate 200. The widths 270-280 and the distance 290 are all measured in the X direction. In an embodiment, the width 270 is in a range from about ¼ to about ⅞ of the width 210 (also shown in FIGS. 6B and 6C) of the gate 200. In an embodiment, the distance 290 is in a range from about 1/16 to about ⅜ of the width 210 of the gate 200. It is understood that the overlapping distance 290 is correlated with the threshold voltage $V_t$ of the transistor device. As the distance 290 varies, so does the threshold voltage $V_t$. In this manner, the threshold voltage $V_t$ is tunable.

In an embodiment, the doping concentration level of the region N0 is less than about $2 \times 10^{18}$ ions/cm$^3$. In an embodiment, the doping concentration level of the region N1 is greater than about $1 \times 10^{19}$ ions/cm$^3$. In an embodiment, the doping concentration level of the region N2 is greater than about $1 \times 10^{20}$ ions/cm$^3$.

A complementary metal oxide semiconductor (CMOS) device implemented according to various aspects of the present disclosure can have both n-FETs and p-FETs on the same chip. For the n-FETs, the work function of the gate structure is closer to the conduction band edge. For the p-FETs, the work function of the gate structure is closer to the valence band edge.

Figure 9:
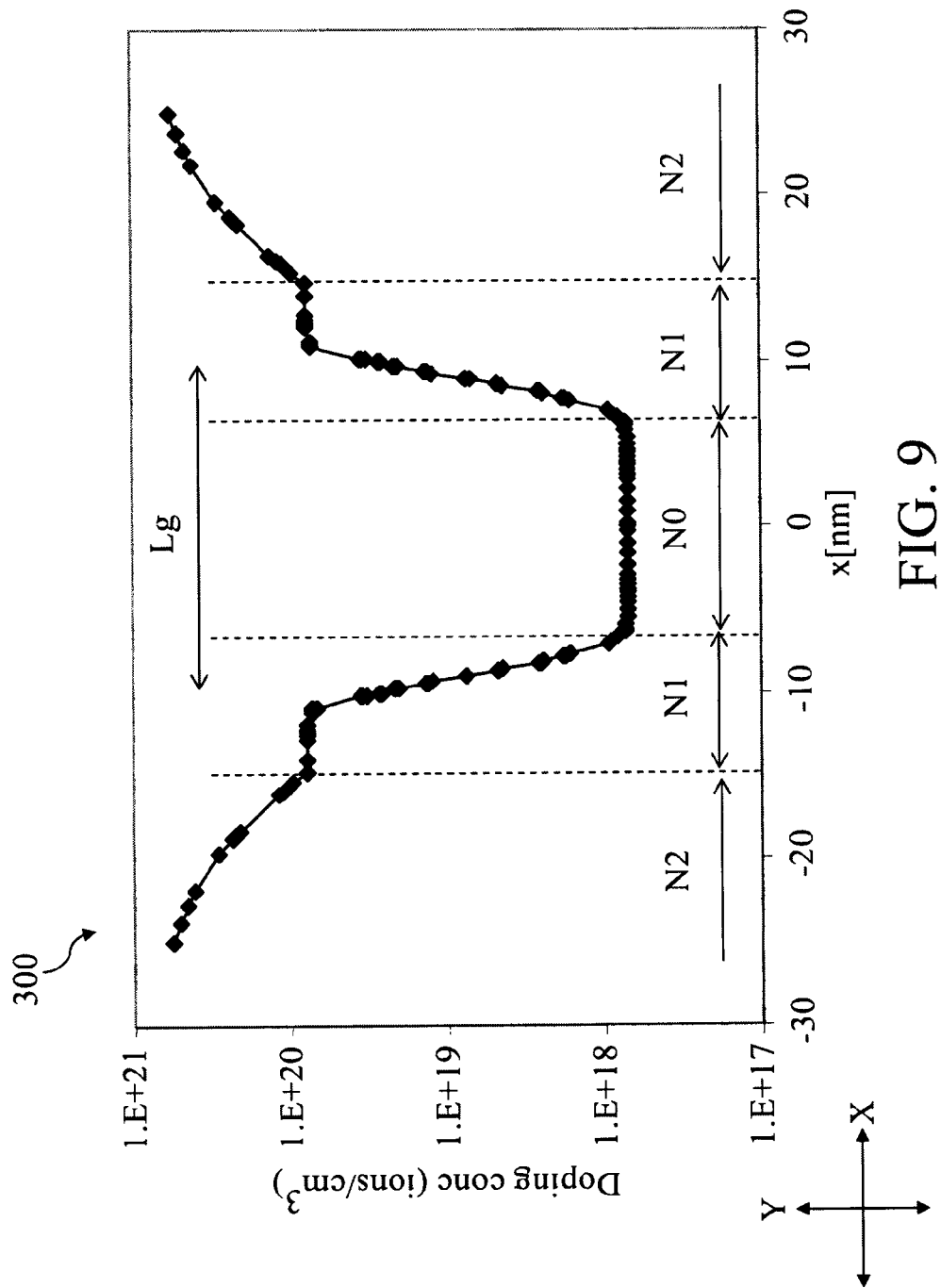
FIG. 9 is a chart plotting doping concentration level versus location.

FIG. 9 is a chart 300 that graphically illustrates how the doping concentration level varies across different locations of the fin structure 150. The chart 300 is a plot of doping concentration level (Y-axis) VS location (X-axis). Note that the Y-axis of the doping concentration level is not the same Y direction discussed above and shown in the preceding Figures. The doping concentration level is measured in units of ions/cm$^3$. The location is measured in units of nanometers. The center of the gate structure 200 (FIG. 8) has a location of 0. Locations to the left of the center of the gate structure 200 has negative units, and the locations to the right of the center of the gate structure 200 has positive units. As is shown in the chart 300, the doping concentration level decreases as the location moves closer to the center of the gate structure 200, and increases as the location moves away from the center of the gate structure 200.

The approximate boundaries of the N0, N1, and N2 regions discussed above are also illustrated in FIG. 9 as broken lines. It can be seen that the doping concentration level of the N0 region is the lowest of the three regions and is at or below about $7.3 \times 10^{17}$ ions/cm$^3$ in the embodiment shown here. The doping concentration level of the N2 region is the highest of the three regions and is at or above about $7.7 \times 10^{19}$ ions/cm$^3$ in the embodiment shown here. The doping concentration level of the N1 region is in the middle of the three regions and is between about $7.3 \times 10^{17}$ ions/cm$^3$ to about $7.7 \times 10^{19}$ ions/cm$^3$ in the embodiment shown here. Once again, FIG. 9 illustrates the non-uniform doping profile of the FinFET device discussed herein.

Although the doping concentration level changes, the dopant polarity remains the same across all three of the regions N0, N1, and N2. In one embodiment, all three regions N0, N1, and N2 are N-type doped. In another embodiment, all three regions N0, N1, and N2 are P-type doped.

The gate length Lg of the FinFET device is also shown in FIG. 9. In an embodiment, the gate length Lg is equivalent to the width 210 (shown in FIG. 8) of the gate structure 200. As FIG. 9 illustrates, the gate length Lg extends beyond the N0 region and into the N1 region. This is consistent with what is shown in FIG. 8 as well.

FIGS. 3A-C, 4A-C, 5A-C, 6A-C, 7A-C, and 8 illustrate a process flow of fabricating a FinFET device according to a silicon-on-insulator (SOI) approach. FIGS. 10A-C, 11A-C, 12A-C, 13A-C, and 14A-C illustrate various cross-sectional views and top views of a FinFET device 100A fabricated according to an alternative embodiment involving using a bulk instead of the SOI approach. For the sake of consistency and clarity, components that are similar to the ones appearing in FIGS. 3A-C, 4A-C, 5A-C, 6A-C, 7A-C, and 8 are labeled the same in FIGS. 10A-C, 11A-C, 12A-C, 13A-C, and 14A-C.

Referring to FIGS. 10A-10C, the semiconductor layer 130 is formed on the substrate 110. Here, instead of including a dielectric material, the substrate 110A includes a doped-silicon material, for example a P-type doped silicon material. The doping polarity of the substrate 110A is opposite than that of the semiconductor layer 130. The substrate 110A is a p-type substrate for an n-FET device, and the substrate 110A is a n-type substrate for a p-FET device.

Referring now to FIGS. 11A-11C, the semiconductor layer 130 is patterned into the elongate fin structure 150. Unlike the previous embodiment shown in FIG. 4, the patterning process also removes a portion of the substrate 110A, as is illustrated in FIG. 11A. Thereafter, an insulating material 400 is formed in place of the removed-portions of the substrate 110A on either side of the fin structure 150. The insulating material 400 may include a dielectric material, for example a silicon oxide material.

Figure 13C:
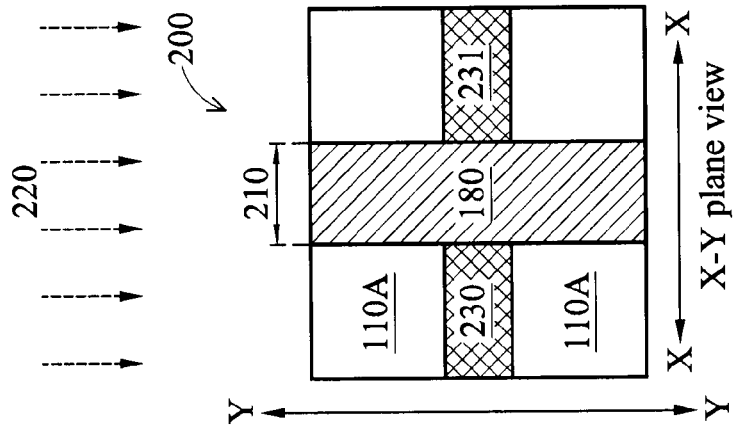
Figure 13B:
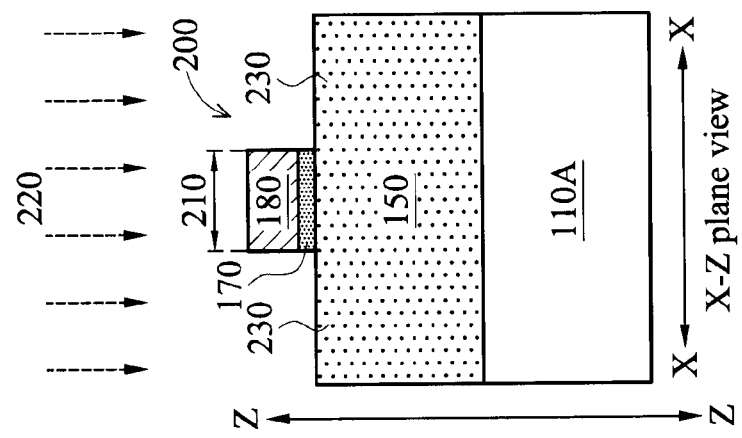
Figure 13A:
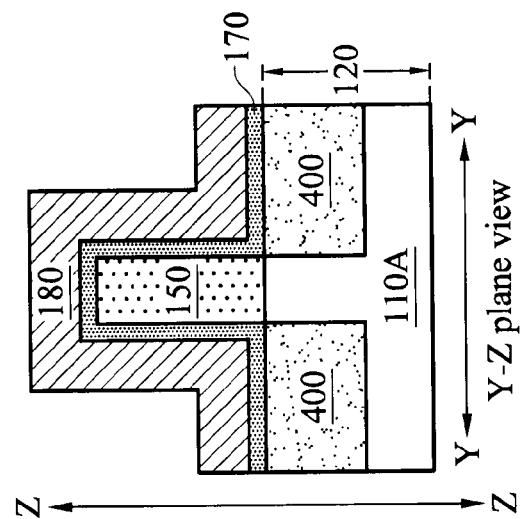
Figure 14C:
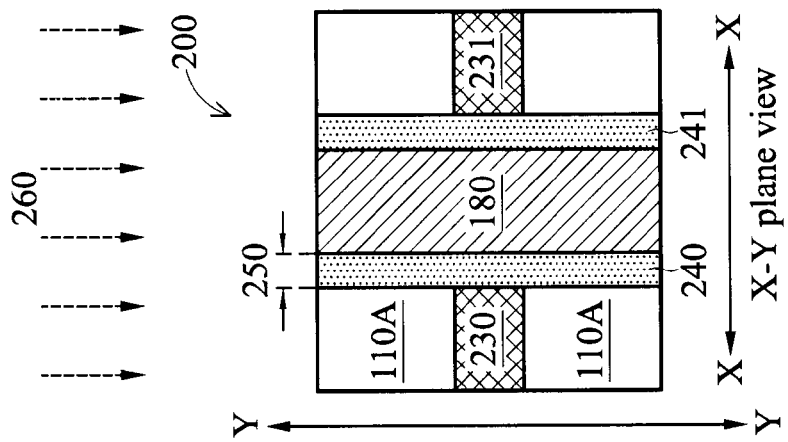
Figure 14B:
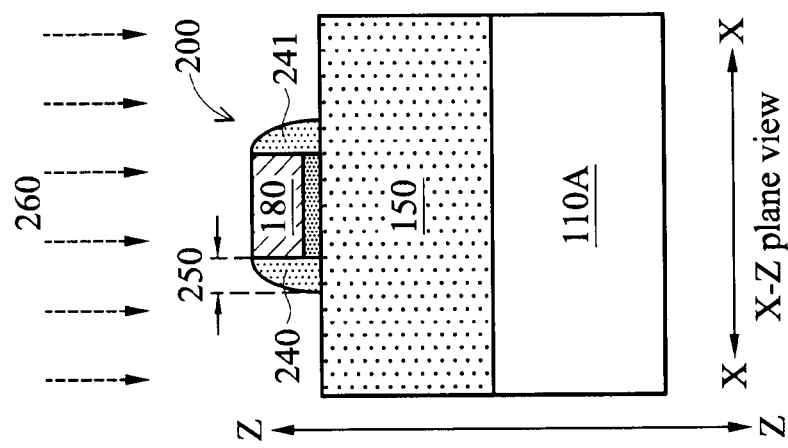
Figure 14A:
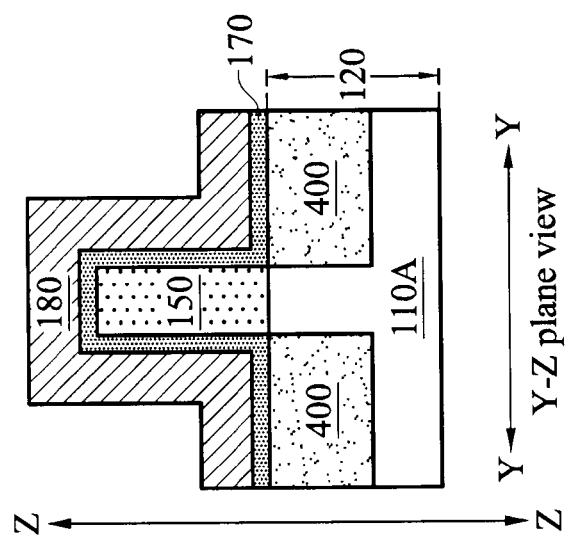

Referring now to FIGS. 12A-12C, the gate electrode layer 180 and the gate dielectric layer 170 are formed over the fin structure 150. Referring now to FIGS. 13A-13C, the gate electrode layer 180 and the gate dielectric layer 170 are patterned to form the gate structure 200. The gate structure 200 wraps around the fin structure 150. After the gate structure 200 is formed, the implantation process 220 is performed to form the source/drain regions 230-231. Referring now to FIGS. 14A-14C, the gate spacers 240 and 241 are formed around the long sides of the gate structure 200. Subsequently, the implantation process 260 is performed to further define the source/drain regions 230-231. An activation annealing process may be performed thereafter. As is the case with the embodiment discussed above in association with FIGS. 3-8, the embodiment shown in FIGS. 10-14 also have a non-uniform doping profile across its fin structure, for example a doping profile similar to that shown in FIG. 9.

Figure 15A:
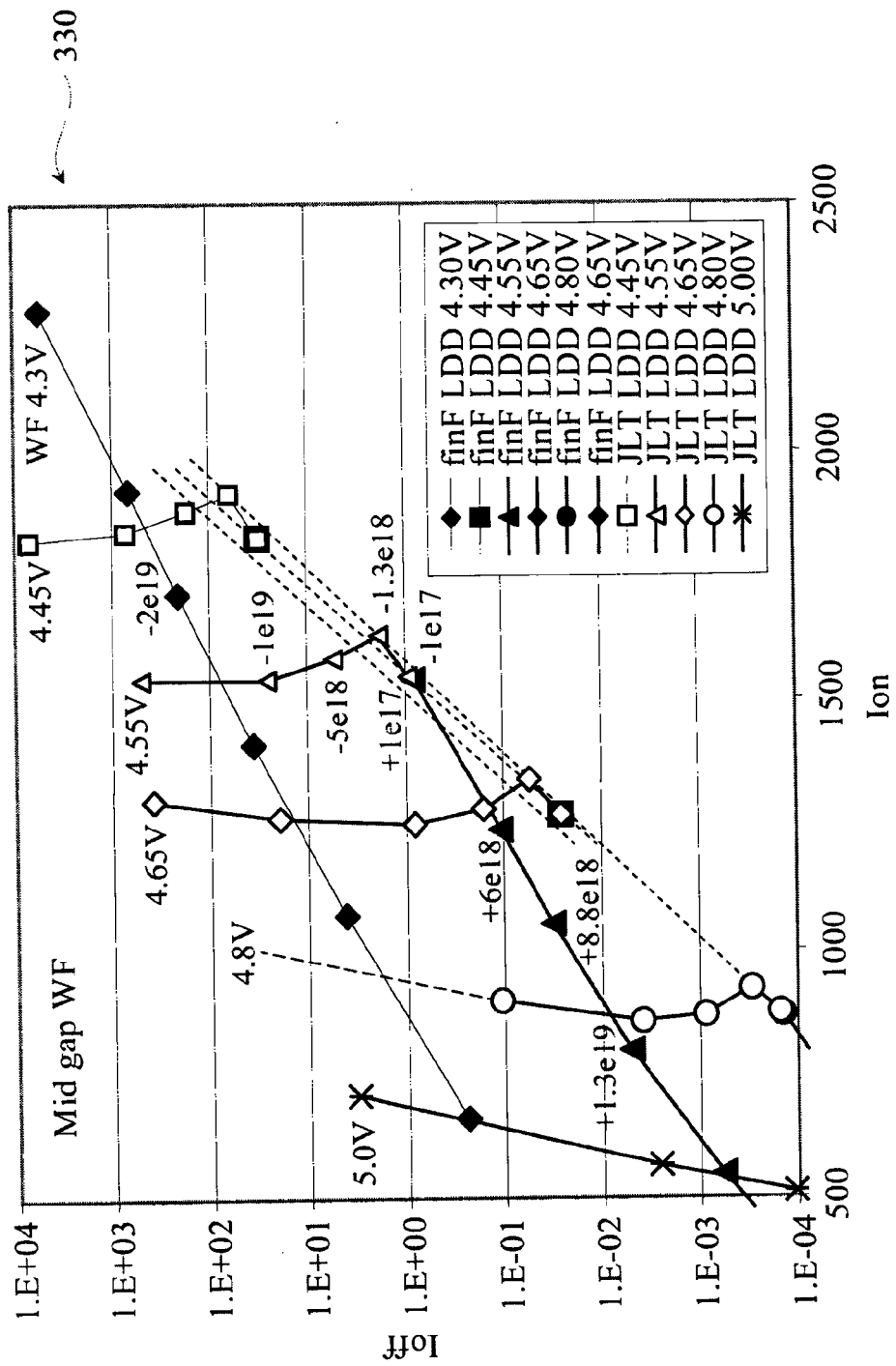
FIG. 15A-15C includes several charts illustrating work function and channel dose optimization.
Figure 15B:
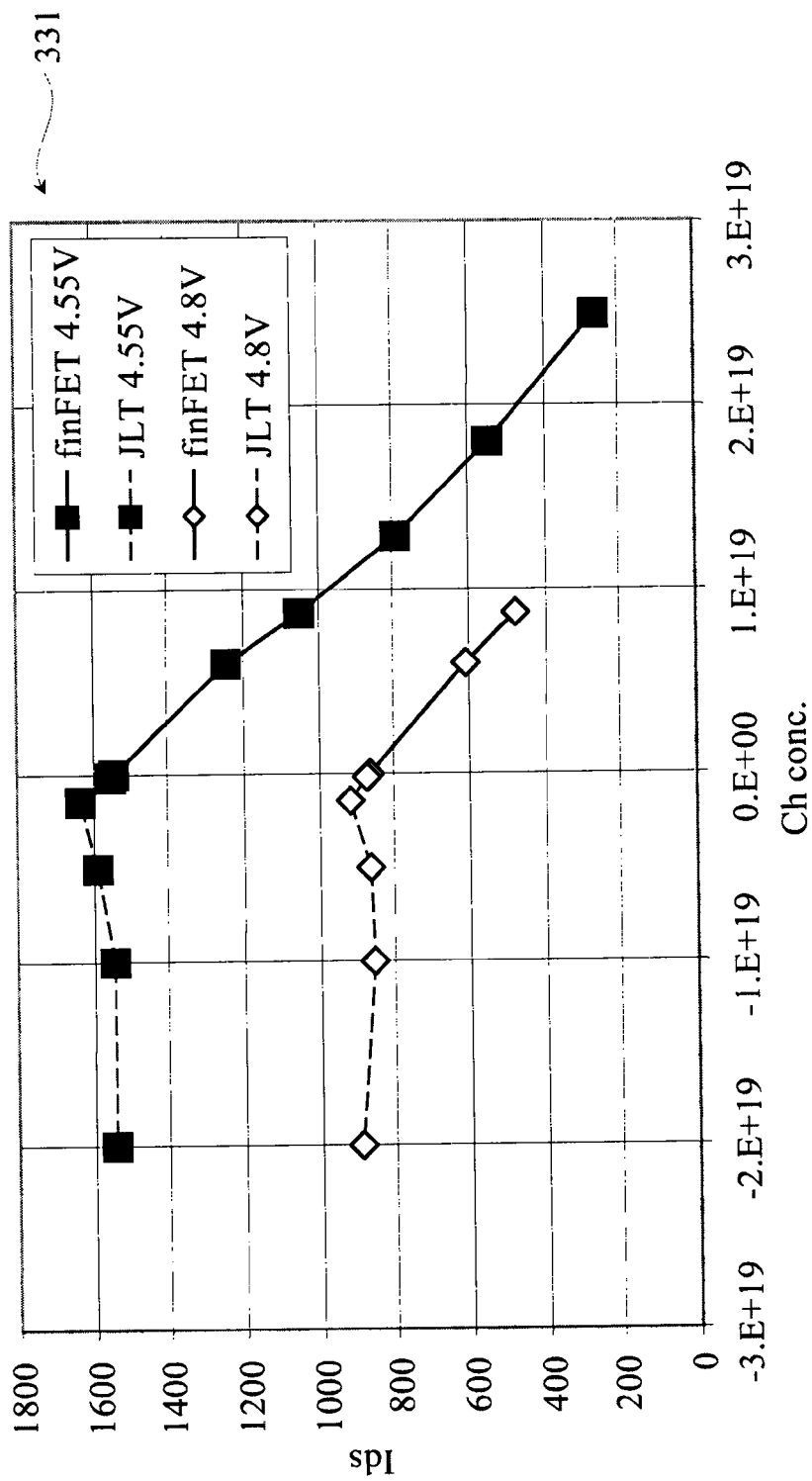
Figure 15C:
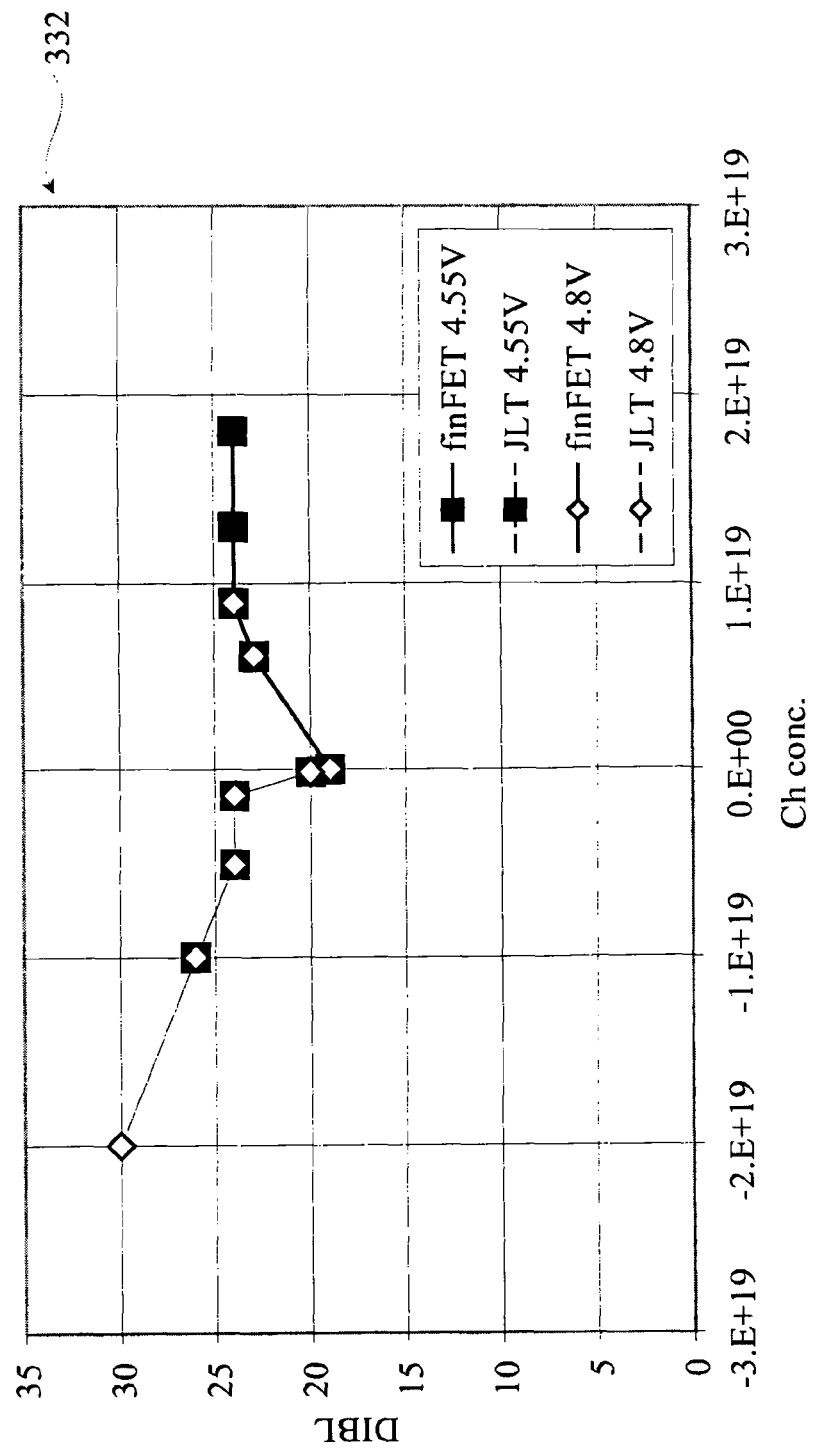

FIGS. 15A-C include several charts 330-332 that illustrate work function and channel dose optimization according to various aspects of the present disclosure. In an embodiment, an optimized point between $I_{on}$ (on-current or drain current) and $I_{off}$ (off-current or leakage current) has an associated channel dose between about 0 and about $-2 \times 10^{19}$.

Table 1 below lists some of the differences between some of the embodiments of the present disclosure and other devices. These other devices may include traditional FinFET devices, or traditional junction-less transistors, and modified junction-less transistors. It is understood that the differences in Table 1 are merely examples and are not meant to be limiting. Additional differences may exist but are not listed in Table for the sake of simplicity.

TABLE 1

| | Certain embodiments of present disclosure | Traditional FinFET devices | Traditional junction-less transistors | Modified junction-less transistors |
|---|---|---|---|---|
| Work function | N-type (4.1 V~4.65 V) | N-type | P-type | P-type |
| Channel | N− | P− | N | N− |
| LDD | N+ | N+ | none | N+ |
| S/D | N++ | N++ | N++ | N++ |

According to Table 1, some of the embodiments of the present disclosure have:

a N-type work function tuned in the range from about 4.1 volts to about 4.65 volts;

an N-type channel that has a low doping concentration level;

an N-type LDD region that has a heavier doping concentration level than the channel; and an N-type S/D region that has a heavier doping concentration level than the LDD region.

The above combination of properties are not found in any of the other devices. For example, the traditional FinFET devices have an oppositely doped channel, the traditional junction-less transistors have a doping concentration level higher than that of the embodiments herein and an LDD region that is not doped. Other differences can be identified by referring to Table 1 above.

Figure 16:
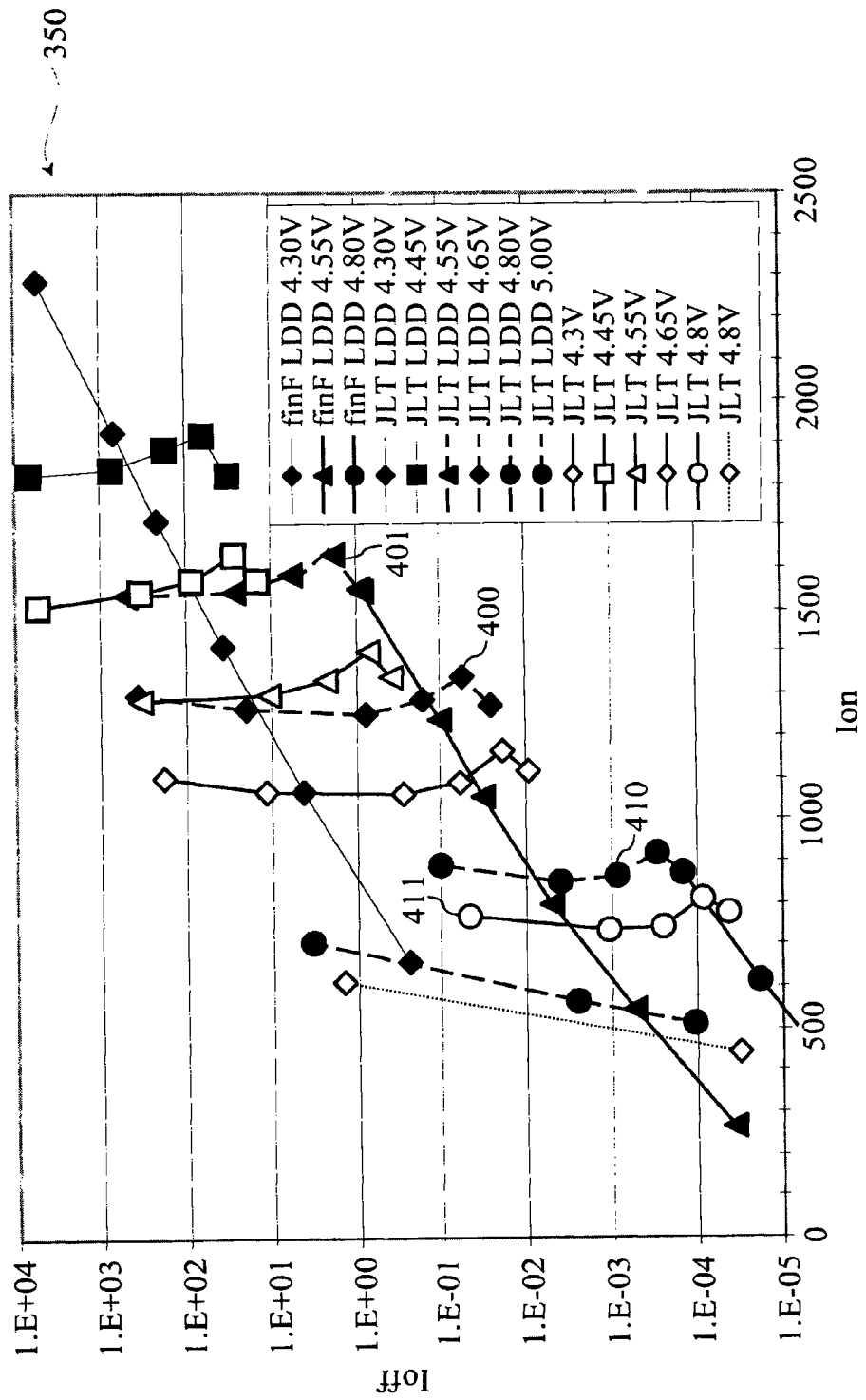
FIG. 16 includes a chart that illustrates $I_{on}$ and $I_{off}$ performances of a device according to an embodiment.

FIG. 16 is another chart 350 that illustrate $I_{on}$ and $I_{off}$ performances of a device according to embodiments of the present disclosure in comparison with the other devices listed in Table 1 above. The chart 350 includes a plurality of sample points, some of which represent $I_{on}$ and $I_{off}$ performances of embodiments of the present disclosure, others of which represent $I_{on}$ and $I_{off}$ performances of other devices. For example, sample points 400 and 401 represent embodiments of the present disclosure, while sample points 410 and 411 represent other devices. It can be seen that the sample points 400 and 401 have better $I_{on}$ and $I_{off}$ performances than the sample points 410 and 411. In other words, the sample points 400 and 401 have good $I_{on}$ current and still maintain low leakage current ($I_{off}$ current).

It is understood that although the Figures discussed above only show a single FinFET device, a plurality of similar FinFET devices may be fabricated on a single wafer or on the same chip. For example, a complementary metal oxide semiconductor (CMOS) device includes both n-FET devices and p-FET devices. Both the n-FET devices and the p-FET devices can be fabricated using the process flow discussed above. In an embodiment, a work function of the gate of an n-FET device is closer to a conduction band edge, and a work function of the gate of a p-FET device is closer to a valence band edge.

The various embodiments of the present disclosure discussed herein offer several advantages, it being understood that other embodiments may offer different advantages, and that no particular advantage is required for any embodiment. One advantage of having such a non-uniform doping profile across the fin structure 150 is reduced parasitic resistance and therefore increased drain current over conventional devices. In some embodiments, the drain current can be increased by at least 20% while leakage current and channel dose are comparable with conventional devices.

One of the broader forms of the present disclosure involves a semiconductor device. The semiconductor device includes: a semiconductor layer disposed over a substrate, the semiconductor layer having a fin structure; a gate structure disposed over the fin structure, the gate structure having a gate dielectric layer and a gate electrode layer, the gate structure wrapping around a portion of the fin structure; and source/drain regions disposed in the fin structure; wherein a doping profile across the fin structure is non-uniform, and wherein a first region of the portion of the fin structure being wrapped around by the gate structure has a lower doping concentration level than the rest of the fin structure.

Another one of the broader forms of the present disclosure involves a FinFET semiconductor device. The FinFET semiconductor device includes: a fin structure formed over a substrate, the substrate including one of: a silicon material and an insulator material; a gate formed in a manner such that it at least partially wraps around a segment of the fin structure; and source/drain regions formed in the fin structure; wherein: the fin structure includes a first portion, a second portion, and a third portion; the first portion is completely wrapped around by the gate; the second portion is at least partially wrapped around by the gate and has a heavier doping concentration level than the first portion; and the third portion is not wrapped around by the gate and has a heavier doping concentration level than second portion.

Yet another one of the broader forms of the present disclosure involves a method of fabricating a semiconductor device. The method includes: forming a semiconductor layer on a substrate; patterning the semiconductor layer into a fin structure; forming a gate dielectric layer and a gate electrode layer over the fin structure; patterning the gate dielectric layer and the gate electrode layer to form a gate structure in a manner so that the gate structure wraps around a portion of the fin structure; and performing a plurality of implantation processes to form source/drain regions in the fin structure, the plurality of implantation processes being carried out in a manner so that a doping profile across the fin structure is non-uniform, and wherein a first region of the portion of the fin structure being wrapped around by the gate structure has a lower doping concentration level than other regions of the fin structure.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of fabricating a semiconductor device, comprising:

forming a semiconductor layer on a substrate;

patterning the semiconductor layer into a fin structure;

forming a gate dielectric layer and a gate electrode layer over the fin structure;

patterning the gate dielectric layer and the gate electrode layer to form a gate structure in a manner so that the gate structure wraps around a portion of the fin structure; and performing a plurality of implantation processes to form source/drain regions in the fin structure, the plurality of implantation processes being carried out in a manner so that a doping profile across the fin structure is non-uniform including a first region having a first doping concentration level, a second region extending from the first region and partially wrapped around by the gate structure and having a second doping concentration level that is different than the first doping concentration level, and a third region extending from the second region but not wrapped around by the gate structure and having a third doping concentration level that is different than the second doping concentration level, wherein the first, second, and third regions all have the same doping polarity.

2. The method of claim 1, wherein the first region and the gate structure have respective first and second lateral dimensions that extend in the same direction, and wherein the first lateral dimension is in a range from about ¼ of the second lateral dimension to about ⅞ of the second lateral dimension.

3. The method of claim 1, wherein the substrate is an insulator substrate.

4. The method of claim 1, wherein the substrate is a bulk silicon substrate, and wherein the bulk silicon substrate and the semiconductor layer are oppositely doped.

5. The method of claim 1, wherein the semiconductor device is an N-type FinFET device, and further including tuning a work function of the gate structure so that the work function is closer to a conduction band edge than to a valence band edge.

6. The method of claim 1, wherein the semiconductor device is a P-type FinFET device, and further including tuning a work function of the gate structure so that the work function is closer to a valence band edge than to a conduction band edge.

7. A method comprising:
forming a fin structure over a semiconductor substrate;
forming a gate structure over the fin structure such that the gate structure at least partially wraps around the fin structure;
forming a first doped region having a dopant type at a first concentration in the fin structure, wherein the first doped region is formed under the gate structure;
forming a second doped region having the dopant type at a second concentration that is different than the first concentration in the fin structure, wherein the second doped region extends laterally within the fin structure from the first doped region under the gate structure to under a spacer on a sidewall of the gate structure; and
forming a third doped region having the dopant type at a third concentration that is different than the second concentration in the fin structure, wherein the third doped region extends laterally within the fin structure from the second doped region under the spacer to beyond an outer edge of the spacer away from the gate structure, wherein the dopant type of the first, second, and third doped regions is the same.

8. The method of claim 7, wherein forming the second doped region having the dopant type at the second concentration includes forming a fourth doped region having the dopant type at the second concentration in the fin structure, wherein the fourth doped region extends laterally within the fin structure from the first doped region under the gate to under another spacer on another sidewall of the gate structure.

9. The method of claim 8, wherein forming the third doped region having the dopant type at the third concentration includes forming a fifth doped region having the dopant type at the third concentration in the fin structure, wherein the fifth doped region extends laterally within the fin structure from the fourth doped region under the another spacer to beyond an outer edge of the another spacer away from the gate structure.

10. The method of claim 7, wherein forming the fin structure over the semiconductor substrate includes removing a portion of the semiconductor substrate to form a recess within the semiconductor substrate adjacent the fin structure.

11. The method of claim 10, further comprising forming an insulating material within the recess adjacent the fin structure.

12. The method of claim 7, wherein the first doped region is a channel region associated with the gate structure;
wherein the second doped region is a lightly doped source/drain region associated with the gate structure, and
wherein the third doped region is a source/drain region associated with the gate structure.

13. A method comprising:
forming a semiconductor layer over a substrate;
forming a first doped region having a dopant type at a first concentration in the semiconductor layer;
patterning the semiconductor layer into a fin structure, wherein the fin structure includes the first doped region;
forming a gate structure over the fin structure such that the gate structure at least partially wraps around the fin structure;
forming a second doped region having the dopant type at a second concentration that is different than the first concentration in the fin structure, wherein the second doped region extends laterally within the fin structure from the first doped region under the gate structure to under a spacer on a sidewall of the gate structure; and
forming a third doped region having the dopant type at a third concentration that is different than the second concentration in the fin structure, wherein the third doped region extends laterally within the fin structure from the second doped region under the spacer to beyond an outer edge of the spacer away from the gate structure, wherein the dopant type of the first, second, and third doped regions is the same.

14. The method of claim 13, wherein the first doped region is directly below the gate structure.

15. The method of claim 13, wherein the third concentration is greater than the second concentration and the second concentration is greater than the first concentration.

16. The method of claim 13, wherein the dopant type is a P-type.

17. The method of claim 13, wherein the dopant type is an N-type.

18. The method of claim 13, forming the spacer on the sidewall of the gate structure after forming the second doped region.

19. The method of claim 1, wherein the third doping concentration level is greater than the second doping concentration level.

20. The method of claim 1, wherein the second doping concentration level is greater than the first doping concentration level.

* * * * *